United States Patent [19]
Aloisi

[11] Patent Number: 5,840,057
[45] Date of Patent: Nov. 24, 1998

[54] DEVICE FOR IONTOPHORETIC PHYSIOTHERAPY WITH FROZEN MEDICAMENT CRYSTALS

[76] Inventor: Alessandro Aloisi, via Colombo 10, 95030 Mascalucia CT, Italy

[21] Appl. No.: 687,528
[22] PCT Filed: Jan. 27, 1995
[86] PCT No.: PCT/IT95/00010
  § 371 Date: Aug. 7, 1996
  § 102(e) Date: Aug. 7, 1996
[87] PCT Pub. No.: WO96/22810
  PCT Pub. Date: Aug. 1, 1996
[51] Int. Cl.$^6$ ........................................... A61N 1/30
[52] U.S. Cl. .............................. 604/20; 607/115
[58] Field of Search .............. 604/20; 607/2–3, 607/115

[56] References Cited

U.S. PATENT DOCUMENTS

| | | | |
|---|---|---|---|
| 2,126,070 | 8/1938 | Wappler | 604/20 |
| 2,493,155 | 1/1950 | McMillan | 604/20 |
| 3,163,166 | 12/1964 | Brant et al. | |
| 4,141,359 | 2/1979 | Jacobsen et al. | 604/20 |
| 4,764,164 | 8/1988 | Sasaki | 604/20 |
| 4,786,278 | 11/1988 | Masaki | 604/20 |
| 5,084,008 | 1/1992 | Phipps | 604/20 |
| 5,135,478 | 8/1992 | Sibalis | 604/20 |
| 5,421,817 | 6/1995 | Liss et al. | 604/20 |
| 5,431,625 | 7/1995 | Fabian et al. | 604/20 |
| 5,571,149 | 11/1996 | Liss et al. | 604/20 |

FOREIGN PATENT DOCUMENTS

| | | |
|---|---|---|
| 292930 | 11/1988 | European Pat. Off. . |
| 8808729 | 11/1988 | European Pat. Off. . |

*Primary Examiner*—Mark Bockelman
*Attorney, Agent, or Firm*—Beveridge, DeGrandi, Weilacher & Young, L.L.P.

[57] ABSTRACT

The device for physiotherapy according to the present invention includes an electric current generator (4) with variable and in case modulated frequency, supplied between two electrodes that comprise the sick anatomic part to be treated, the first electrode being of a container (2–5) for a medicament solution in distillate water brought to the freezing point, and the other one in an element (6) with a wide surface that may be applied to the skin for closing the electric circuit, through the passage of the current through the anatomic part, consisting of the flow of ions coming from the frozen medicament crystals, so that nearly the whole of said ions penetrate through the anatomic part being treated, directly reaching the activity areas.

12 Claims, 3 Drawing Sheets

DEVICE FOR IONTOPHORETIC PHYSIOTHERAPY WITH FROZEN MEDICAMENT CRYSTALS

The present invention concerns a device for physiotherapy comprising means for the realization of iontophoresis with medicament crystals frozen at temperatures between 0° C. and −5° C.

It is already well known that the electrophoresis (or iontophoresis) process consists of in the local penetration through the skin of the patients of medicament ions, in distillate water solutions, by means of the passage of electric currents between two electrodes applied to the part to be treated.

This known process, however, shows many limits and contraindications:

only medicaments that dissociate into ions may be used in solution;

when there is a considerable current intensity, burns and/or abrasions of the skin may occur;

the quantity of medicament in ions that can pass through the skin and therefore be active is a minimum percentage of the whole, so that the doses cannot be computed precisely due to the dispersion of the special sponges; and when the medicament passes through the Ph-value of the skin gets altered, also according to the sweating level of the patient reacting to contact with the electrode.

It is the aim of the present invention to eliminate or reduce the above mentioned contraindications by means of a combination of the electrophoresis with the method of the cryotherapy, which at present is used for local lowering of the temperature in traumatized parts.

The aim set forth is reached by means of the device for physiotherapy according to the present invention, comprising an electric current generator with variable and in case modulated frequency, supplied between two electrodes that comprise the sick anatomic part to be treated, the first electrode consisting of a container for a medicament solution in distillate water brought to the freezing point, and the other one in an element with a wide surface that may be applied to the skin for closing the electric circuit, by means of the passage of the current through the anatomic part, consisting of the flow of ions coming from the frozen medicament crystals, so that nearly the whole of the ions penetrate through the anatomic part being treated, directly reaching the activity areas.

The advantages of the device according to the present invention are many and considerable:

the electrode with the frozen medicament crystal ions may be connected, by means of a contact provided in the container, to the cathode as well as to the anode, according to the polarity of the ions;

the lubrication caused by the progressive melting of the medicament ice on the skin allows the circulation of a current intensity higher than the one of the conventional iontophoresis, without causing burns or other;

the medicament can be exactly dosed and in a constant quantity for the whole treatment, as all ions and only those present in the crystal are translated into the electric current, while the pure melted solvent will be collected while running down the skin;

because of the lubrication due to the manual massage performed by the operator onto the skin with the ionic frozen crystal, any Ph-value alteration of the skin is prevented;

the process may be applied also in the presence of a laceration and contusion trauma, as no burn and/or abrasion occurs; and an immediate analgesic effect takes place, as the medicament in ion-crystals is kept at a temperature of about −5° C. during the treatment, making the ions penetrate in the deepest structures of the anatomic parts.

The device and the process according to the present invention may be applied to all cases of local treatment of pathologies that may be treated with active ions, and in particular in the following cases:

scapular and humeral periarthritis;

post-operating trauma and/or with intra-articular effusion of the knee;

insertion trauma;

tendinitis, inguinal tendinitis, coxo-arthrosis, etc.; and peripherical neurological syndrome.

The present invention will be described in detail hereinbelow with reference to the drawings in which a preferred embodiment is shown, and in which.

Figure 1:
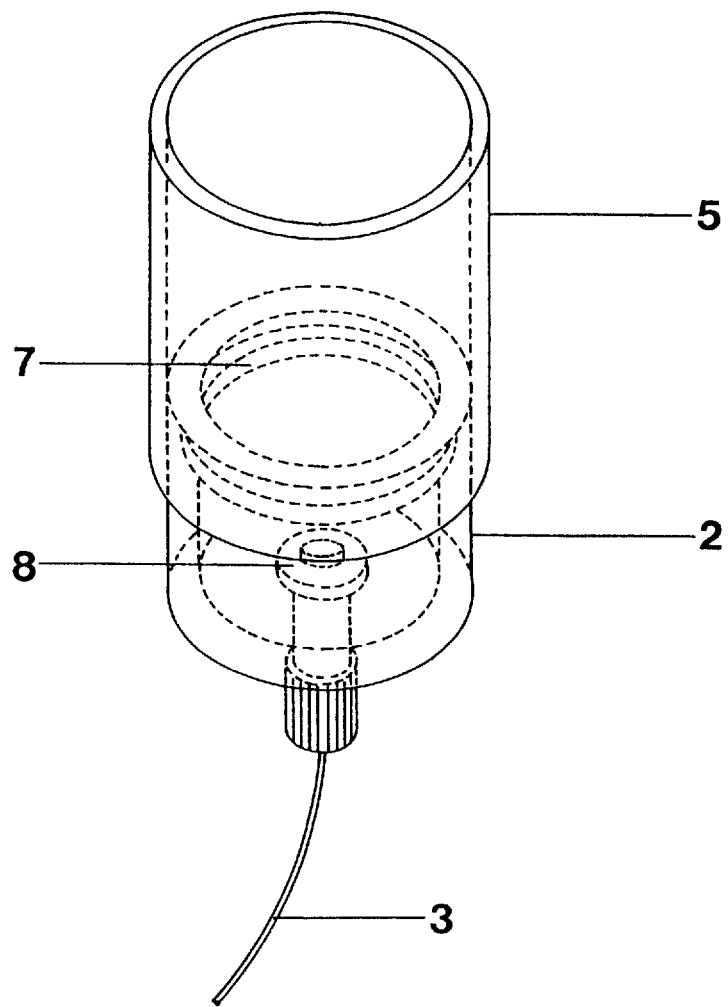
FIG. 1 shows, in an axonometric and transparency view, the container for the medicament in distillate water, with the internal contact for the electric connection.
Figure 2:
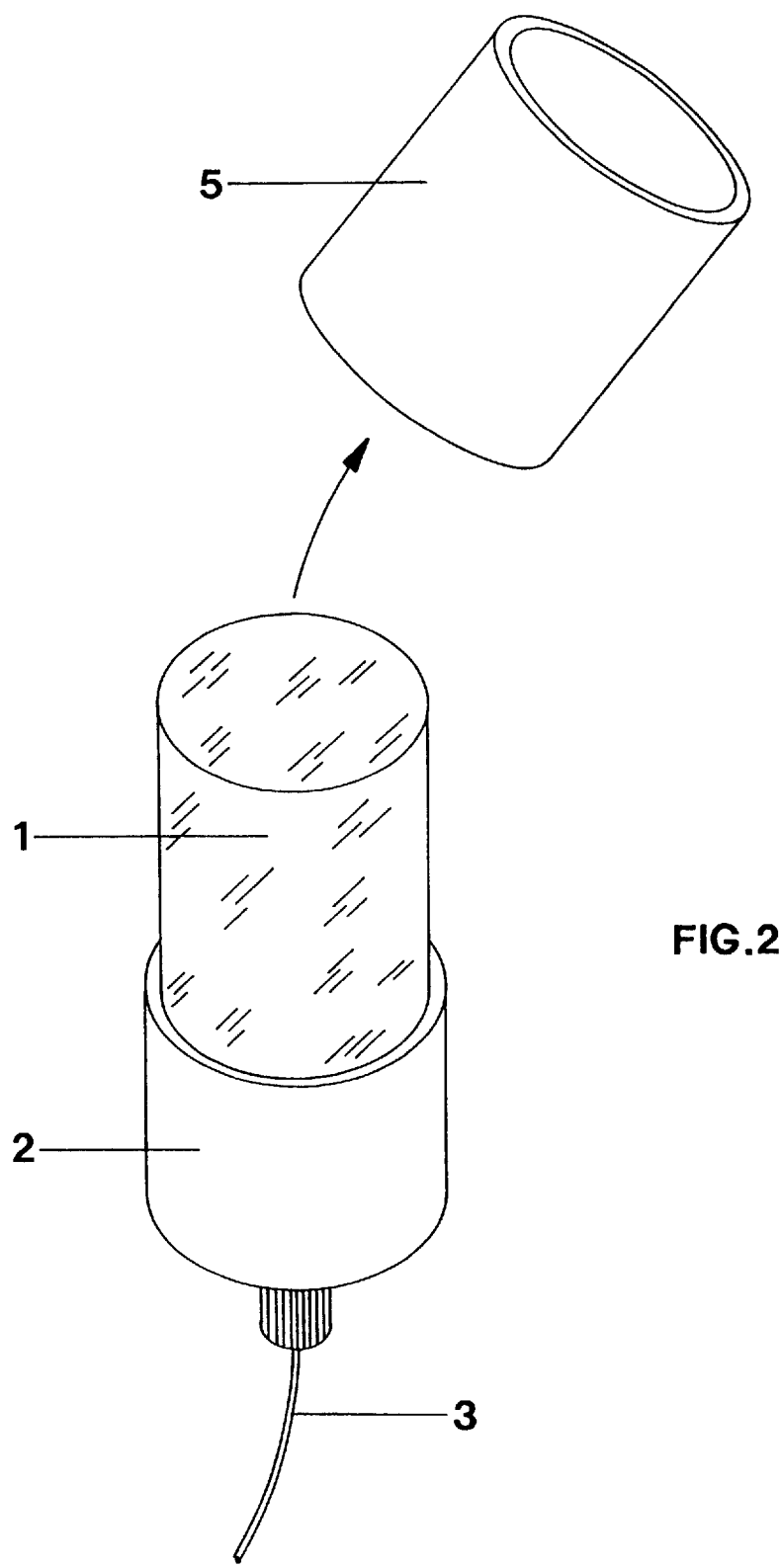
FIG. 2 shows the structure of the electrode, consisting of the medicament frozen to ion crystals, without the upper part of the container.
Figure 3:
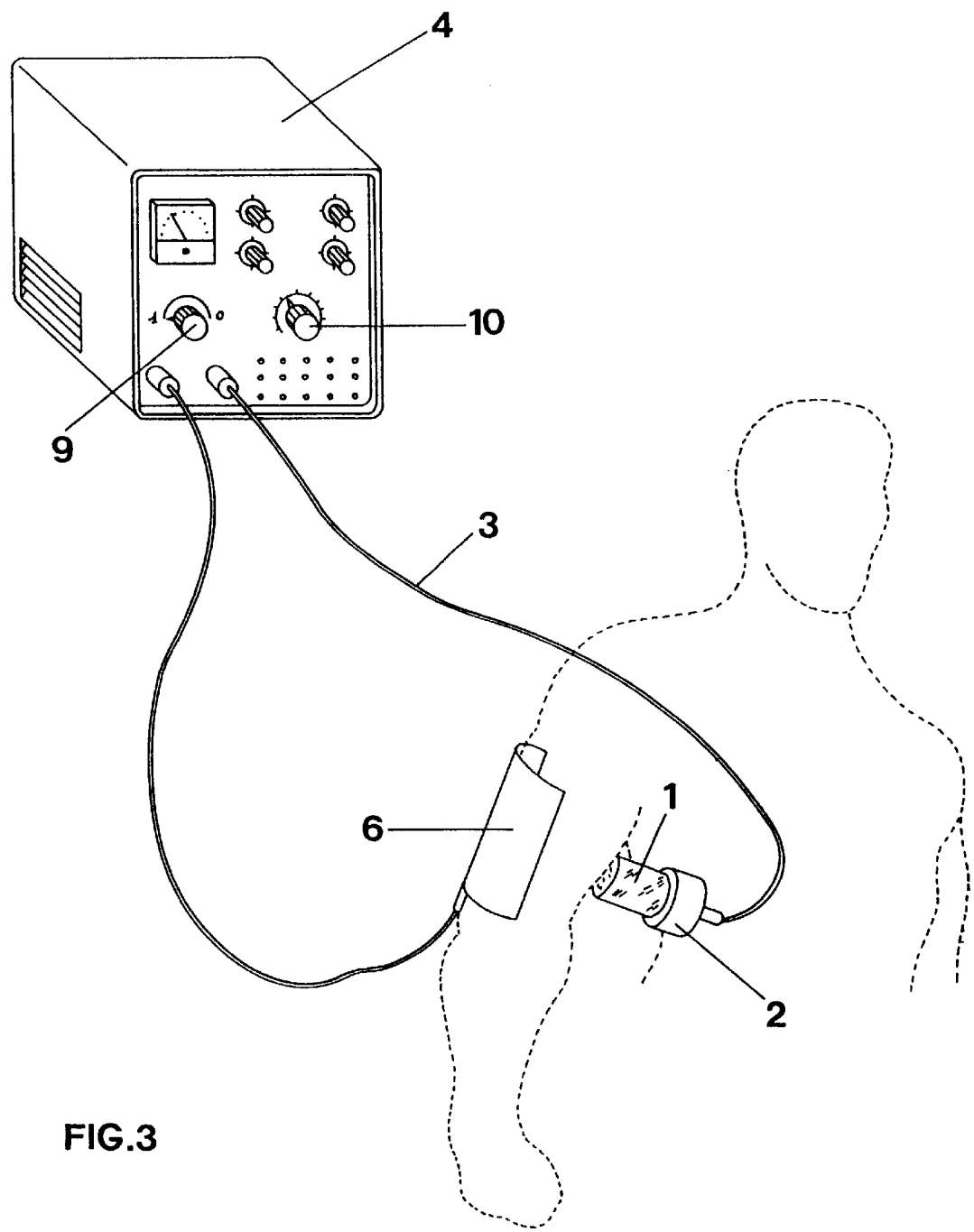
FIG. 3 shows the electric and functional scheme of the complete device.

The figures show the device for iontophoretic physiotherapy with frozen medicament crystals, comprising:

an electrode 1, positive or negative according to the sign of the ions into which the medicament in solution will dissociate, consisting of a container divided in a lower part 2, into which reaches the cable 3 of the electric generator, and an upper part 5, connected with a joint or in any other way, for increasing the capacity and for being removed, after the solidification of the ionic solution of the medicament in a low temperature ambient, so as to form a head for the emission of ions between 0° and −5° C., and to be kept into contact, manually by the operator, on the patient's skin;

an apparatus 4, generating periodical currents, triangular, sinusoidal or of other kinds, single-phase or two-phase, in case modulated in width and/or in frequency, for supplying the energy for the transport of the frozen medicament ions on the head, in a closed circuit;

an electrode 6 with a sign opposite to electrode 1, connected to apparatus 4, that provides for the passage of the ionic current through the anatomic part to be treated, consisting of an element with a wide surface that may be applied, with the interposition of gel or other electric contact means, onto the patient's skin.

The process for applying the device according to the present invention may be described as follows:

the medicament is given into a solution, getting electrolytically ionized;

the container is filled up, with the upper part 5 with the lower part 2 and provided with means 7, grooves or similar, for mechanically keeping the head emitting ions once the contained medicament is solidified in a freezer, and with a pin 8 or similar, projecting inside the lower part 2 for establishing a good electric contact with the ion ice-block, forming the electrode 1;

the upper part 5 of the container is removed, so as to uncover the frozen electrode 1;

the anatomic part to be treated is shortly massaged with the frozen electrode head 1, for getting the patient used to the low temperature;

electrode 6 is applied to a contraposed part of the body;

1 switch 9 is pushed so as to determine the closing of the electric circuit of apparatus 4 as well as the passage of the local current, where the intensity of the current may be adjusted with knob 10; and the frozen ionized medicament is kept at a temperature of about −5° C., making the medicament penetrate into the deepest structures of the anatomic part treated.

I claim:

1. An iontophoretic physiotherapy device comprising;

an electrode holder holding a frozen medicament crystal electrode containing a frozen medicament wherein the frozen medicament crystal electrode is to be placed on a first area of the skin of a patient, wide surface electrode electrode is adapted to be placed on a second area of the skin of a patient, and an apparatus for generating a periodical electrical current through the frozen medicament crystal electrode and the electrode.

2. The iontophoretic physiotherapy device of claim 1, wherein the periodical current is triangular or sinusoidal and is modulated in width or in frequency.

3. The iontophoretic physiotherapy device of claim 2, wherein the periodical current is single phase or two phase.

4. The iontophoretic physiotherapy device of claim 1 wherein the electrode holder further comprises;

a container, the container having a lower part and a pin passing through the lower part, and an upper part detachably connected to the lower part wherein the container is adapted to form a frozen medicament crystal electrode by pouring a medicament solution into the container and freezing the solution.

5. The iontophoretic physiotherapy device of claim 4 wherein the lower part of the container is provided with a means for keeping the frozen medicament crystal electrode in the electrode holder.

6. A method of delivering medicament ions to a patient with the iontophoretic physiotherapy device of claim 1 comprising;

placing the frozen medicament crystal electrode onto a first area of skin of a patient in need of treatment, placing the electrode onto a second area of skin of the patient, and generating a periodical current through the frozen medicament crystal electrode and the electrode to deliver medicament ions through the skin of the patient.

7. The method of claim 6 further comprising;

lowering the temperature of the first area of skin.

8. The method of claim 7 wherein the treatment is for a condition selected from the group consisting of scapular periarthritis, humeral periarthritis, post operative trauma, intra-articular effusion of the knee, post operative trauma with intra-articular effusion of the knee, insertion trauma, tendinitis, inguinal tendinitis, coxo-arthrosis, and peripheral neurological syndrome.

9. The method of claim 7 performed in the presence of contusion or laceration trauma.

10. The iontophorectic physiotherapy device according to claim 1 further comprising;

a container, the container having a lower part and a pin passing through the lower part, and an upper part detachably connected to the lower part wherein the container is adapted to form the frozen medicament crystal electrode by pouring a medicament solution into the container and freezing the solution.

11. The iontophoretic physiotherapy device of claim 10 wherein the lower part of the container is provided with a means for keeping the frozen medicament crystal electrode in the electrode holder.

12. The iontophoretic physiotherapy device of claim 11 wherein the lower part of the container is in the form of a cylinder with an interior and an exterior and wherein groves are formed in the interior of the lower part of the container as the means for keeping the frozen medicament crystal electrode in the electrode holder.

* * * * *